(12) United States Patent
Steenfeldt-Jensen et al.

(10) Patent No.: US 8,632,506 B2
(45) Date of Patent: Jan. 21, 2014

(54) MEDICAL DELIVERY SYSTEM COMPRISING A CODING MECHANISM

(75) Inventors: Søren Steenfeldt-Jensen, Hornbaek (DK); Thomas Pedersen, Helsingoer (DK); Michael Ejstrup Hansen, Morud (DK)

(73) Assignee: Novo Nordisk A/S, Bagsvaerd (DK)

(*) Notice: Subject to any disclaimer, the term of this patent is extended or adjusted under 35 U.S.C. 154(b) by 531 days.

(21) Appl. No.: 12/305,684

(22) PCT Filed: Jun. 29, 2007

(86) PCT No.: PCT/EP2007/056594
§ 371 (c)(1),
(2), (4) Date: Mar. 11, 2009

(87) PCT Pub. No.: WO2008/000827
PCT Pub. Date: Jan. 3, 2008

(65) Prior Publication Data
US 2010/0152657 A1      Jun. 17, 2010

Related U.S. Application Data

(60) Provisional application No. 60/830,505, filed on Jul. 13, 2006, provisional application No. 60/899,058, filed on Feb. 2, 2007.

(30) Foreign Application Priority Data

Jun. 30, 2006  (EP) .................................... 06013586
Jan. 10, 2007  (EP) .................................... 07000429

(51) Int. Cl.
*A61M 5/00*  (2006.01)
(52) U.S. Cl.
USPC ........................................ 604/208; 604/211
(58) Field of Classification Search
USPC ................................................ 604/208, 407
See application file for complete search history.

(56) References Cited

U.S. PATENT DOCUMENTS

| 31,873 | A | 4/1861 | Cramer |
| 31,878 | A | 4/1861 | Downer |
| 1,594,493 | A | 8/1926 | Brown |

(Continued)

FOREIGN PATENT DOCUMENTS

| CH | 0315980 | 9/1956 |
| CH | 0501411 | 1/1971 |
| DE | 2137405 | 2/1973 |
| DE | 44 19 235 | 12/1995 |
| DE | 20110690 | 9/2001 |

(Continued)

OTHER PUBLICATIONS

Search Report from International Application No. PCT/EP2007/062661, mailed Feb. 25, 2008.
English language abstract for DE2137405.
English language abstract for DE4419235.
English language abstract for CH0315980.

(Continued)

*Primary Examiner* — Nicholas Lucchesi
*Assistant Examiner* — Jenna Zhang
(74) *Attorney, Agent, or Firm* — Wesley A. Nicolas; Marc A. Began; Reza Green

(57) ABSTRACT

A medical delivery system comprising a container (202) for accommodation of a medicament and a dosing assembly (204) adapted to be fastened to the container. The medical delivery system comprises a coding mechanism for ensuring that only a predetermined container can be fastened to a predetermined dosing assembly. A container for use in the medical delivery system. A dosing assembly for use in the medical delivery system.

24 Claims, 7 Drawing Sheets

(56) References Cited

U.S. PATENT DOCUMENTS

Figure 1:
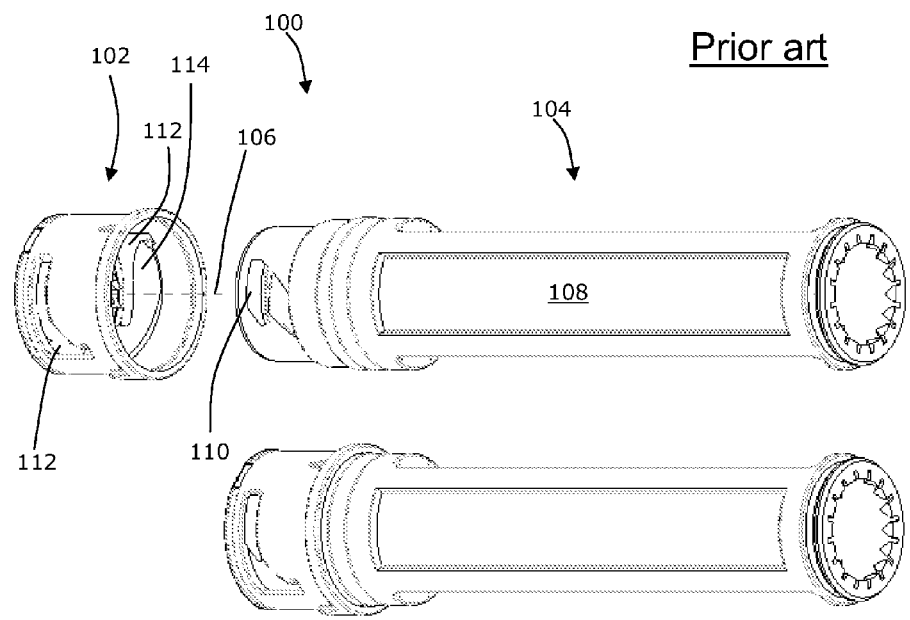

| | | | |
|---|---|---|---|
| 2,020,828 A | 11/1935 | Goldberg | |
| 2,707,466 A | 5/1955 | Hoskins | |
| 2,818,864 A | 1/1958 | Hudson | |
| 2,865,372 A | 12/1958 | Miskel et al. | |
| 2,880,723 A | 4/1959 | Adams | |
| 2,888,924 A | 6/1959 | Dunmire | |
| 3,021,840 A | 2/1962 | Hallamore et al. | |
| 3,130,724 A | 4/1964 | Higgins et al. | |
| 3,130,742 A | 4/1964 | Higgins et al. | |
| 3,170,667 A | 2/1965 | Szohatzky | |
| 3,336,924 A | 8/1967 | Sarnoff et al. | |
| 3,375,825 A | 4/1968 | Keller | |
| 3,820,652 A | 6/1974 | Thackston | |
| 3,831,599 A | 8/1974 | Needham | |
| 3,895,633 A | 7/1975 | Bertner et al. | |
| 3,916,893 A | 11/1975 | De Felice | |
| 3,989,044 A | 11/1976 | Meierhoefer | |
| 4,089,432 A | 5/1978 | Crankshaw | |
| 4,150,673 A | 4/1979 | Watt | |
| 4,280,723 A | 7/1981 | Moldestad | |
| 4,490,142 A | 12/1984 | Silvern | |
| 4,592,745 A | 6/1986 | Rex et al. | |
| 4,619,640 A | 10/1986 | Potolsky et al. | |
| 4,619,651 A | 10/1986 | Kopfer et al. | |
| 4,664,656 A | 5/1987 | Taddei | |
| 4,685,314 A | 8/1987 | Greenwalt et al. | |
| 4,693,833 A | 9/1987 | Toshikuni et al. | |
| 4,740,205 A | 4/1988 | Seltzer et al. | |
| 4,768,568 A | 9/1988 | Fournier et al. | |
| 4,781,701 A | 11/1988 | Geprags | |
| 4,944,736 A | 7/1990 | Holtz | |
| 4,948,000 A | 8/1990 | Grobenkort | |
| 4,973,318 A | 11/1990 | Holm et al. | |
| 4,976,701 A | 12/1990 | Ejlersen et al. | |
| 5,000,744 A | 3/1991 | Hoffman et al. | |
| 5,002,537 A | 3/1991 | Hoffman et al. | |
| 5,017,190 A | 5/1991 | Simon et al. | |
| 5,084,017 A * | 1/1992 | Maffetone | 604/110 |
| 5,205,833 A | 4/1993 | Harsh et al. | |
| 5,226,896 A | 7/1993 | Harris | |
| 5,244,465 A | 9/1993 | Michel | |
| 5,269,317 A | 12/1993 | Bennett | |
| 5,286,258 A | 2/1994 | Haber et al. | |
| 5,458,580 A | 10/1995 | Hajishoreh | |
| 5,478,323 A | 12/1995 | Westwood et al. | |
| 5,498,253 A | 3/1996 | Aswad et al. | |
| 5,554,134 A | 9/1996 | Bonnichsen | |
| 5,584,815 A | 12/1996 | Pawelka et al. | |
| 5,611,783 A | 3/1997 | Mikkelsen | |
| 5,693,027 A | 12/1997 | Hansen et al. | |
| 5,743,889 A | 4/1998 | Sams | |
| 5,938,642 A * | 8/1999 | Burroughs et al. | 604/208 |
| 5,954,700 A | 9/1999 | Kovelman | |
| 5,957,896 A * | 9/1999 | Bendek et al. | 604/207 |
| 6,017,330 A | 1/2000 | Hitchins et al. | |
| 6,197,040 B1 * | 3/2001 | LeVaughn et al. | 606/182 |
| 6,582,399 B1 | 6/2003 | Smith et al. | |
| 6,582,408 B1 | 6/2003 | Buch-Rasmussen et al. | |
| 6,648,859 B2 | 11/2003 | Bitdiner et al. | |
| 7,604,619 B2 | 10/2009 | Eich et al. | |
| 2001/0047153 A1 | 11/2001 | Trocki et al. | |
| 2002/0016571 A1 | 2/2002 | Kirchhofer et al. | |
| 2002/0099360 A1 | 7/2002 | Bierman | |
| 2002/0169470 A1 * | 11/2002 | Kuhr et al. | 606/182 |
| 2003/0004466 A1 | 1/2003 | Bidtiner et al. | |
| 2003/0078195 A1 * | 4/2003 | Kristensen et al. | 514/3 |
| 2004/0210199 A1 | 10/2004 | Atterbury et al. | |
| 2004/0215152 A1 | 10/2004 | Kirchhofer et al. | |
| 2004/0238776 A1 | 12/2004 | Peters et al. | |
| 2006/0153693 A1 | 7/2006 | Fiechter et al. | |
| 2008/0051713 A1 | 2/2008 | Kohlbrenner | |

FOREIGN PATENT DOCUMENTS

| | | |
|---|---|---|
| EP | 217055 | 4/1987 |
| EP | 0 549 694 | 7/1993 |
| EP | 549694 | 6/1995 |
| EP | 762311 | 3/1997 |
| EP | 774270 | 5/1997 |
| EP | 897729 | 2/1999 |
| EP | 897728 | 5/2003 |
| GB | 301961 | 12/1928 |
| GB | 1205201 | 9/1970 |
| GB | 1437595 | 5/1976 |
| GB | 1525455 | 9/1978 |
| GB | 2 214 819 | 9/1989 |
| WO | WO89/02760 | 4/1989 |
| WO | WO 90/09202 | 8/1990 |
| WO | WO92/04926 | 4/1992 |
| WO | WO98/47559 | 10/1998 |
| WO | WO98/56438 | 12/1998 |
| WO | WO00/02605 | 1/2000 |
| WO | WO00/35519 | 6/2000 |
| WO | WO 01/72361 | 10/2001 |
| WO | WO 02/30490 | 4/2002 |
| WO | WO 03/011372 | 2/2003 |
| WO | WO 03/011373 | 2/2003 |
| WO | WO 03/017915 | 3/2003 |
| WO | WO 2006/069456 | 7/2006 |
| WO | WO 2008/009646 | 1/2008 |

OTHER PUBLICATIONS

English language abstract for CH0501411.
Non-final Office Action mailed on Feb. 1, 2010 in U.S. Appl. No. 12/374,600, filed Jan. 21, 2009 by Christiansen et al.
Non-final Office Action mailed on Jan. 19, 2010 in U.S. Appl. No. 12/373,339, filed Jan. 12, 2009, by Hansen et al.
English Language Abstract of German Patent No. 20110690, published on Sep. 13, 2001 obtained from Derwent Patent Database.
Novo Nordisk Product Brochure for Insuject-X 1987.
Non-Final Office Action Mailed Apr. 9, 2004 in U.S. Appl. No. 10/230,428, filed Aug. 23, 2002; First Named Inventor: Kristensen.
Non-Final Office Action Mailed Nov. 18, 2004 in U.S. Appl. No. 10/230,428, filed Aug. 23, 2002; First Named Inventor: Kristensen.
Notice of Allowance Mailed May 19, 2005 in U.S. Appl. No. 10/230,428, filed Aug. 23, 2002; First Named Inventor: Kristensen.
Non-Final Office Action Mailed Feb. 9, 2006 in U.S. Appl. No. 10/230,428, filed Aug. 23, 2002; First Named Inventor: Kristensen.
Notice of Allowance Mailed Oct. 10, 2006 in U.S. Appl. No. 10/230,428, filed Aug. 23, 2002; First Named Inventor: Kristensen.
Non-Final Office Action Mailed Dec. 12, 2006 in U.S. Appl. No. 10/230,428, filed Aug. 23, 2002; First Named Inventor: Kristensen.
Non-Final Office Action Mailed Feb. 10, 2009 in U.S. Appl. No. 11/784,738, filed Apr. 9, 2007; First Named Inventor Kristensen.
Final Office Action Mailed Jun. 2, 2009 in U.S. Appl. No. 11/784,738, filed Apr. 9, 2007; First Named Inventor Kristensen.
Final Office Action Mailed Aug. 12, 2010 in U.S. Appl. No. filed Sep. 2, 2009; First Named Inventor: Kristensen.
Notice of Allowance Mailed Dec. 13, 2010 in U.S. Appl. No. filed Sep. 2, 2009; First Named Inventor: Kristensen.
Final Action Mailed Jul. 30, 2010 in U.S. Appl. No. 12/373,339, filed Jan. 12, 2009 by Hansen.
Non-Final Office Action Mailed Nov. 24, 2010 in U.S. Appl. No. 12/373,339, filed Jan. 12, 2009 by Hansen.
Non-Final Office Action Mailed Feb. 18, 2011 in U.S. Appl. No. 12/373,340, filed Jan. 12, 2009 by Christiansen.
Non-Final Office Action Mailed Feb. 17, 2011 in U.S. Appl. No. 12/357,013, filed Jan. 21, 2009 by Christiansen.
Final Office Action Mailed Jul. 15, 2010 in U.S. Appl. No. 12/374,600, filed Jan. 21, 2009 by Christiansen.
Non-Final Office Action Mailed Mar. 4, 2011 in U.S. Appl. No. 12/374,600, filed Jan. 21, 2009 by Christiansen.

* cited by examiner

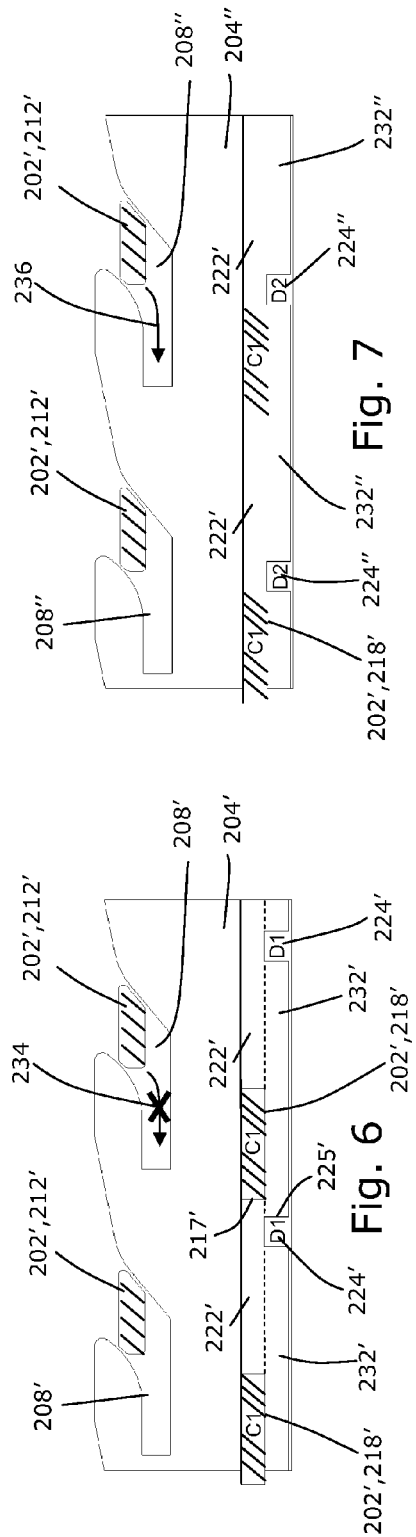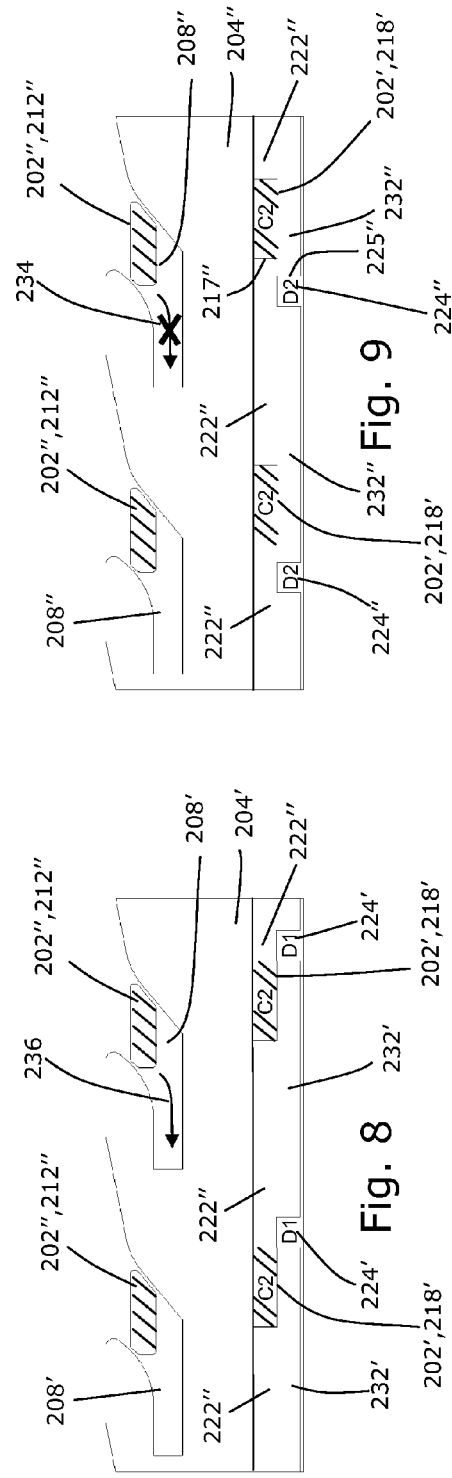

MEDICAL DELIVERY SYSTEM COMPRISING A CODING MECHANISM

CROSS-REFERENCE TO RELATED APPLICATIONS

This application is a 35 U.S.C. §371 national stage application of International Patent Application PCT/EP2007/056594 (published as WO 2008/000827), filed Jun. 29, 2007, which claimed priority of European Patent Applications 06013586.0, filed Jun. 30, 2006 and 0700429.6, filed Jan. 10, 2007; this application further claims priority under 35 U.S.C §119 of U.S. Provisional Applications 60/830,505, filed Jul. 13, 2006 and 60/899,058, filed Feb. 2, 2007.

FIELD OF THE INVENTION

The present invention relates to a medical delivery system comprising a container for accommodation of a medicament and a dosing assembly adapted to be fastened to the container. In particular the present invention relates to a medical delivery system comprising a coding mechanism for ensuring that only a predetermined container can be fastened to the dosing assembly.

BACKGROUND OF THE INVENTION

Generally, in order to provide superior medication delivery devices which are likely to be well received by particular groups of patients, a greater diversity in drug delivery systems have been launched to the benefit of patients. As the number of commercially available delivery systems increase, numerous different types of medication holding cartridges or containers are distributed. Most of these types of containers differ in various aspects.

Each medicament container may be filled with a particular type of medicament selected from a large variety of different medicaments, but also different kinds of the same class of medicament (e.g. rapid or long acting insulin) and different concentrations of each particular medicament may be accommodated in the containers.

Moreover, different container volumes may be introduced in order to customize each container, and, thus, the delivery system to the needs of particular users. Variation of container volume may be provided by changing the length or diameter of the container. These modifications usually imply corresponding modifications of the dosing assembly of a medication delivery system, so as to provide a particular stroke of a driving element for expelling the medicament from the container or to provide optimal dosing precision. Further discrimination between different medicament containers may be occasioned by the design requirements for each particular delivery system, such as required sliding friction of the piston accommodated in the container.

In order to discriminate between a larger variety of available containers, numerous container coding systems have been developed which primarily relies on the electronic reading and recognition of specific containers in order to allow delivery of a specific type of a medicament by a dedicated delivery device. The following mechanical coding systems are known in the art:

U.S. Pat. No. 5,611,783 relates to a pen shaped syringe comprising a distal part which may comprise an ampoule and a proximal part containing a dose setting and drive mechanism. The proximal and distal parts have interlocking bayonet coupling means. Protrusions may be provided to form a pattern ensuring that a certain distal part may only be used in connection with a certain proximal part.

WO 03/017915 A1 discloses a cartridge having a distal end provided with a mechanical coding. The mechanical coding has the form of a circular protrusion where the circular outer diameter is dedicated a specific concentration of insulin contained in the cartridge.

U.S. Pat. No. 5,693,027 discloses a plastic top for adapting a standard cartridge to a chosen syringe. The plastic top may be provided with means for keyed engagement with corresponding means in a syringe to keep it unrotatable when mounted with a cartridge in the syringe. In some types of syringes such keyed engagement between cartridge and syringe is further used to ensure that only a certain type of cartridge is used.

U.S. Pat. No. 6,648,859 B2 discloses a drug cartridge assembly for use with a reusable pen body assembly of a medication delivery pen. In order to eliminate cross-use the pen body assembly and the drug cartridge are keyed i.e. they may be threadedly engaged by corresponding threads and grooves, bayonet threads, and grooves, snap fits or a pair of lugs that mate in reverse Luer-Lock manner. The mating members are selected so as to prevent cross-use with other assemblies, e.g., the pitch of the threads may be angled so as to mate only with one another and not with other assemblies.

Yet another prior art system is described in DE 201 10 690.

It is an object of a preferred embodiment of the present invention to provide an alternative to the known systems. Furthermore, it is an object of a preferred embodiment of the present invention to provide a medication delivery system with a large number of possible coding geometries.

Moreover, it is an object of a preferred embodiment of the present invention to provide at least two independent coding levels. Additionally, it is an object of a preferred embodiment of the present invention to provide two redundant coding systems such that if a first fails the other one ensures that only predetermined containers may be fastened to predetermined dosing assemblies. Furthermore, it is an object of a preferred embodiment of the present invention to provide a coding system wherein the user experiences substantially the same operational fastening movement when the container and dosing assembly of a predetermined medical delivery system are coupled/uncoupled to each other regardless of the specific choice among sets of compatible containers and dosing assemblies. Additionally, it is an object of a preferred embodiment of the present invention to provide a system having a large number of differently coded containers/dosing assemblies while simultaneously obtaining a rugged system where the possibility of mechanical failure is minimized Furthermore, it is an object of a preferred embodiment of the present invention to provide an intuitive fastening mechanism for fastening the container to the dosing assembly.

SHORT DESCRIPTION OF THE INVENTION

In a FIRST aspect the present invention relates to a medical delivery system comprising:
  a container adapted to contain a medicament in a chamber defined by the container and a slidably arranged piston which is moveable in a distal direction towards an outlet so as to reduce the volume of the chamber and expel the medicament through the outlet;
  a dosing assembly adapted to be fastened to the container, so as to allow a driver of the dosing assembly to move the piston of the container in the distal direction;
  wherein the dosing assembly defines a first fastening means which during fastening of the container to the dosing assembly engages a second fastening means of the container whereby the container is fastened to the dosing assembly through a predetermined movement defined by at least one of the first and the second fastening means, at least a part of said predetermined movement being a concurrent axial and rotational movement which is less than one revolution;

wherein a sidewall of one of the first and second fastening means defines at least one projection extending in a radial direction, each of the at least one protrusion being adapted to engage a corresponding groove defined in a sidewall of the other one of the first and second fastening means;

wherein a first coding mechanism is defined by a coding geometry of each of the first and the second fastening means, the first coding mechanism being adapted to prevent said predetermined movement unless each of the first and the second fastening means defines a predetermined coding geometry; and wherein the coding geometry is selected from a predetermined group of coding geometries.

The medical system according to the present invention improves user safety as only predetermined containers may be attached to the dosing assembly. Thus, the dosing assembly may be designated to be used with a predetermined kind and/or concentration of a medicament whereby containers accommodating other concentrations or types of medicaments cannot be attached to the dosing assembly.

In the context of the present invention the term "medical delivery system" shall be understood as any system capable of administering a medicament-containing flowable drug. Examples of medical delivery systems are infusion pump applications, dosers, pen-shaped dosers, motor-dosers, and automated syringes such as the AutoPen™.

The invention is applicable to all kinds of medicament delivery devices capable of delivering a medicament to a user from a container which is adapted to be coupled to a dosing assembly of the delivery device. The delivery device may include any delivery device for transcutaneous, subcutaneous, intravenous, intra muscular or pulmonary administration of a drug.

As used herein, the term "medicament" is meant to encompass any medicament-containing flowable drug capable of being passed through a delivery means such as a hollow needle in a controlled manner, such as a liquid, solution, gel or fine suspension. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The chamber of the container may be defined by one or more sidewalls of the container and the slidably arranged piston. In most embodiments at least a part of the container is ring-shaped and defines a cylindrical cavity in which the piston is received. The distal end of the container may comprise a seal for penetration by a cannula so as to allow a medicament contained in the chamber to be expelled through the cannula. The distal end of the container may be adapted to be attached to a holder holding a cannula. As an example the distal end of the container may comprise a thread adapted to cooperate with a corresponding thread of the holder so as to allow the holder to be screwed onto the container.

The outlet of the container may be adapted to cooperate with a needle hub or an infusion set, or any other fluid communicating conduit e.g. defined by a cannula or a needle, adapted to provide fluid access to a medicament accommodated in the container.

The driver of the dosing assembly may comprise a piston rod adapted to move the piston in the distal direction. The piston rod may comprise an element which is more rigid than the piston and is adapted to abut at least a part of and preferably most of the proximal facing surface of the piston whereby a force applied by the piston rod to the rigid element is applied to a larger area of the proximal surface of the piston than if the piston rod had engaged the piston directly.

The dosing assembly defines a first fastening means which during fastening of the container to the dosing assembly engages a second fastening means of the container. In one embodiment a proximal facing surface of the first fastening means of the dosing assembly engages a distal facing surface of the second fastening means of the container.

The container may be fastened to the dosing assembly through a predetermined movement comprising at least a concurrent axial and rotational movement, such as a helical movement. The rotational movement incurred by the concurrent axial and rotational movement is less than one revolution, such as less than 120 degrees, such as less than 90 degrees, such as less than 60 degrees. When the proximal facing surface of the first fastening means and the distal facing surface of the second fastening means are brought into engagement, rotation of the container relative to the dosing assembly causes the container and the dosing assembly to be pulled towards each other.

In a first embodiment the first fastening means of the dosing assembly defines a groove adapted to receive a projection defined by the second fastening means of the container. During fastening of the container to the dosing assembly, a substantially proximal facing surface of the first fastening means of the dosing assembly engages a substantially distal facing surface of the container. The predetermined movement is defined by the shape of at least one of the engaging surfaces. In a further embodiment, the second fastening means defines a plurality of projections such as two, three or four, and the first fastening means defines a corresponding plurality of grooves adapted to be engaged by the projections.

In a second embodiment the groove(s) is/are defined by the container and the projection(s) is/are defined by the dosing assembly. In a third embodiment the container defines a combination of grooves and projections adapted to be engaged by corresponding projections and grooves defined by the dosing assembly.

The coding geometry of the first and second fastening means are adapted to prevent the predetermined movement unless the coding geometries define predetermined coding geometries. The coding geometry may be defined by the axial extent and/or position of at least one of first and the second fastening means, and/or the radial extent of at least one of the first and second fastening means, and/or the circumferential extent and/or position of at least one of the first and second fastening means. Alternatively, or as a supplement, the coding geometry may be defined by the number of coding geometries, i.e. the number of distinctly cooperating fastening means.

The medical device may comprise a second coding mechanism defined by a proximal surface of the container and a corresponding distal surface of the dosing assembly, the proximal end surface of the container may define one or more axially extending protrusions and/or indentations which during fastening of the container to the dosing assembly cooperate(s) with matching one or more protrusions and/or indentations of a distal facing coding surface of the dosing assembly so as to prevent said predetermined movement unless each of the distal and proximal facing surfaces define one or more predetermined protrusions and/or indentations selected from a predetermined group of protrusions and/or indentations. The proximal surface may be a proximal end surface. The distal surface may by a distal end surface. In one embodiment the end surface may be ring-shaped.

In the context of the present invention the terms "groove" and "projection" are only used in connection with the first coding mechanism, and "indentation" and "protrusion" are only used in connection with the second coding mechanism. However, "groove" and "indentation" shall be seen as synonyms and "protrusion" and "projection" shall be seen as synonyms.

The first and second coding mechanisms may be redundant such that if one of said coding mechanisms fails, the other one ensures that only predetermined containers and dosing assemblies can be fastened to each other. Accordingly, an extra level of security is provided. Alternatively, the first and second coding mechanisms may be independent of each other whereby the container can only be attached to the dosing assembly if both the first and second coding mechanisms match.

In one embodiment the first coding mechanism is used to designate a first predetermined feature of the medicament such as its kind, and the second coding mechanism is used to designate a second predetermined feature of the medicament such as its concentration. Other examples of features which the first and/or second coding mechanism may be used to designate are: male/female medication; child/adult medication; prophylactic/therapeutic medication, slow/fast acting medication.

The second coding mechanism may be defined by the circumferential position of the protrusion(s)/indentation(s) and/or the axial extent of the protrusion(s)/indentation(s) and/or the radial extent of the protrusion(s)/indentation(s) and/or the circumferential extent of the protrusion(s)/indentation(s). In one embodiment at least one of the circumferential position, the axial, radial and circumferential extents is used to designate a first feature of the medicament while at least one of the remaining of the circumferential position, the axial, radial and circumferential extents are used to designate a second feature of the medicament.

As an example the position of the indentations may be used to designate the kind of medicament and at least one of the radial, axial or circumferential extents may be used to designate the concentration of the medicament.

In one embodiment the container comprises at least two protrusions, such as two, three or four, extending from the proximal end surface of the container and the dosing assembly comprises at least two indentations, such as two, three or four, adapted to cooperate with the at least two protrusions.

In one embodiment the predetermined movement defines a substantially pure axial movement and a subsequent combined concurrent axial and rotational movement. The substantially pure axial movement may be used to indicate to the user that the projection and the groove match, whereby it may be prevented that a user performs the combined movement with force causing the groove or the projection to be damaged.

Alternatively, or as a supplement, the predetermined movement defines the combined concurrent axial and rotational movement and a subsequent substantially pure rotational movement. The substantially pure rotational movement may be used to indicate to the user that the container and the dosing assembly are in fact fastened to each other.

The first and/or second coding mechanism(s) may be adapted to prevent at least a part of the axial and/or rotational movement of the predetermined movement, so as to prevent coupling of the container to the dosing assembly. When the container cannot be coupled to the dosing assembly, the dosing assembly cannot be used to expel the medicament.

The coding geometry of the first coding mechanism is defined by one or more of: a circumferential extent of the first and second fastening means; an axial extent of the first and second fastening means, the radial extent of the first and second fastening means and the position of the first and second fastening means.

In one embodiment the container comprises a cartridge holder and a cartridge defining said chamber. The second fastening means may be defined by or attached to the cartridge holder. Moreover, the indentation(s)/protrusion(s) may be defined by the cartridge holder. The cartridge and the cartridge holder may be two separate elements, and the cartridge may be frictionally retained in the cartridge holder. In one embodiment the cartridge is made of glass and the cartridge holder is made of a non-glass material for protecting the glass cartridge. The cartridge may be non-removably retained in the cartridge holder, such that if the cartridge is removed from the cartridge holder it cannot be reattached by hand and without tools. This provides the advantage that the cartridge holder cannot be reused when the cartridge has been emptied, accordingly a cartridge with a wrong medicament cannot be inserted into the cartridge holder and be dispensed by use of the dosing assembly. The cartridge holder and the cartridge may define a monolithic element, i.e. forming one element without seams. Such a monolithic element may be formed as a moulded article made of a synthetic resin such as Topas® or polypropylene. Such a moulded article may include the fastening and coding elements which are formed during moulding. However, any material which is suitable for long-term storage of the specific medication to be accommodated in the container may be used.

In one embodiment the medical delivery system comprises a first container adapted to be fastened to a first dosing assembly and a second container adapted to be fastened to a second dosing assembly. Moreover, the first and/or second coding mechanism of at least two of the first and second container and the first and second dosing mechanism may be adapted to prevent the first dosing assembly and second container from being fastened to each other, and to prevent the second dosing assembly and the first container from being fastened to a plurality of different dosing assemblies and a corresponding plurality of dedicated containers forming a group of containers may be provided where each dosing assembly accepts only one specific container selected from the group of containers, wherein the predetermined movement required for coupling and uncoupling containers from its corresponding dosing assembly is the same for all the different dosing assemblies/containers. In this way, patients having several different dosing assemblies will remain confident in using all the devices, as these devices share one and the same common user interface.

The coding features of the container may be sensed by a dosing assembly having electro-mechanical detection of the mechanical features of the cartridge (e.g. electric switches sensing mechanical features, optical detection of mechanical features). Also, in delivery devices primarily based on container sensing making use of "purely" electronically based container recognition methods, the inclusion of the mechanical coding system of the present invention provides significant safety features—either providing redundancy in the coding recognition or providing a potentially larger number of distinctly coded containers.

In a SECOND aspect the present invention relates to a container for a medical delivery system, the container being adapted to contain a medicament in a chamber defined by the container and a slidably arranged piston which is moveable in a distal direction towards an outlet so as to reduce the volume of the chamber and expel the medicament through the outlet, wherein:

the container comprises a fastening means for fastening the container to a dosing assembly by engaging corresponding fastening means of the dosing assembly, so as to allow a driver of the dosing assembly to move the piston of the container in the distal direction;

the fastening means of the container defines one or more projections and/or grooves extending in a radial direction and being shaped so as to allow the container to be fastened to the dosing assembly through a predetermined movement, at least a part of said predetermined movement comprising a concurrent axial and rotational movement which is less than one revolution; and the fastening means of the container defines a coding geometry adapted to prevent said predetermined movement unless the fastening means defines a predetermined coding geometry selected from a predetermined group of coding geometries.

It will be appreciated that the invention according to the second aspect may comprise any feature and/or element of the invention according to the first aspect of the invention.

In a THIRD aspect the present invention relates to a dosing assembly for a medical delivery system, the dosing assembly comprising:

a driver;

a fastening means for fastening the dosing assembly to a container for accommodation of a medicament by engaging corresponding fastening means of the container, so as to allow the driver of the dosing assembly to move a piston of the container in the distal direction;

wherein the fastening means of the dosing assembly defines one or more protrusions and/or indentations extending in a radial direction and being shaped so as to allow the container to be fastened to the dosing assembly through a predetermined movement, at least a part of said predetermined movement comprising a concurrent axial and rotational movement which is less than one revolution;

wherein the fastening means of the dosing assembly defines a coding geometry adapted to prevent said predetermined movement unless the fastening means defines a predetermined coding geometry selected from a predetermined group of coding geometries.

It will be appreciated that the invention according to the third aspect may comprise any feature and/or element of the invention according to the first aspect of the invention.

DETAILED DESCRIPTION OF THE INVENTION

Figure 2:
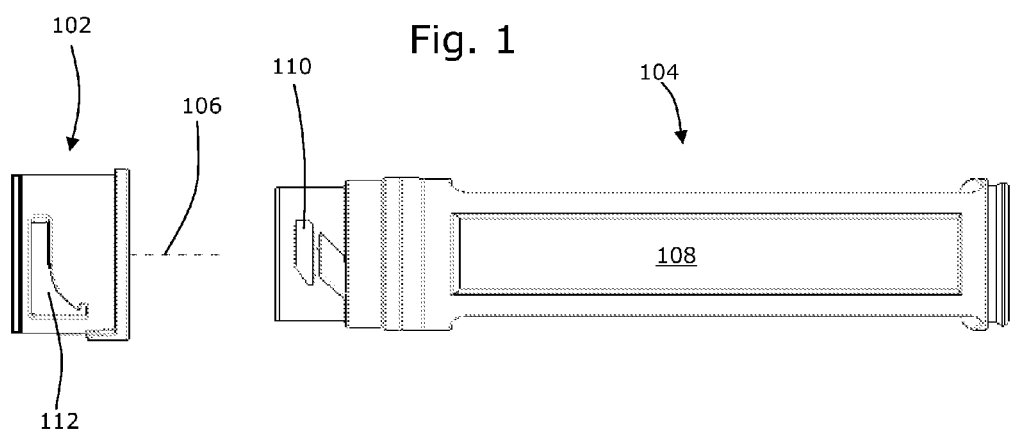
Figure 3:
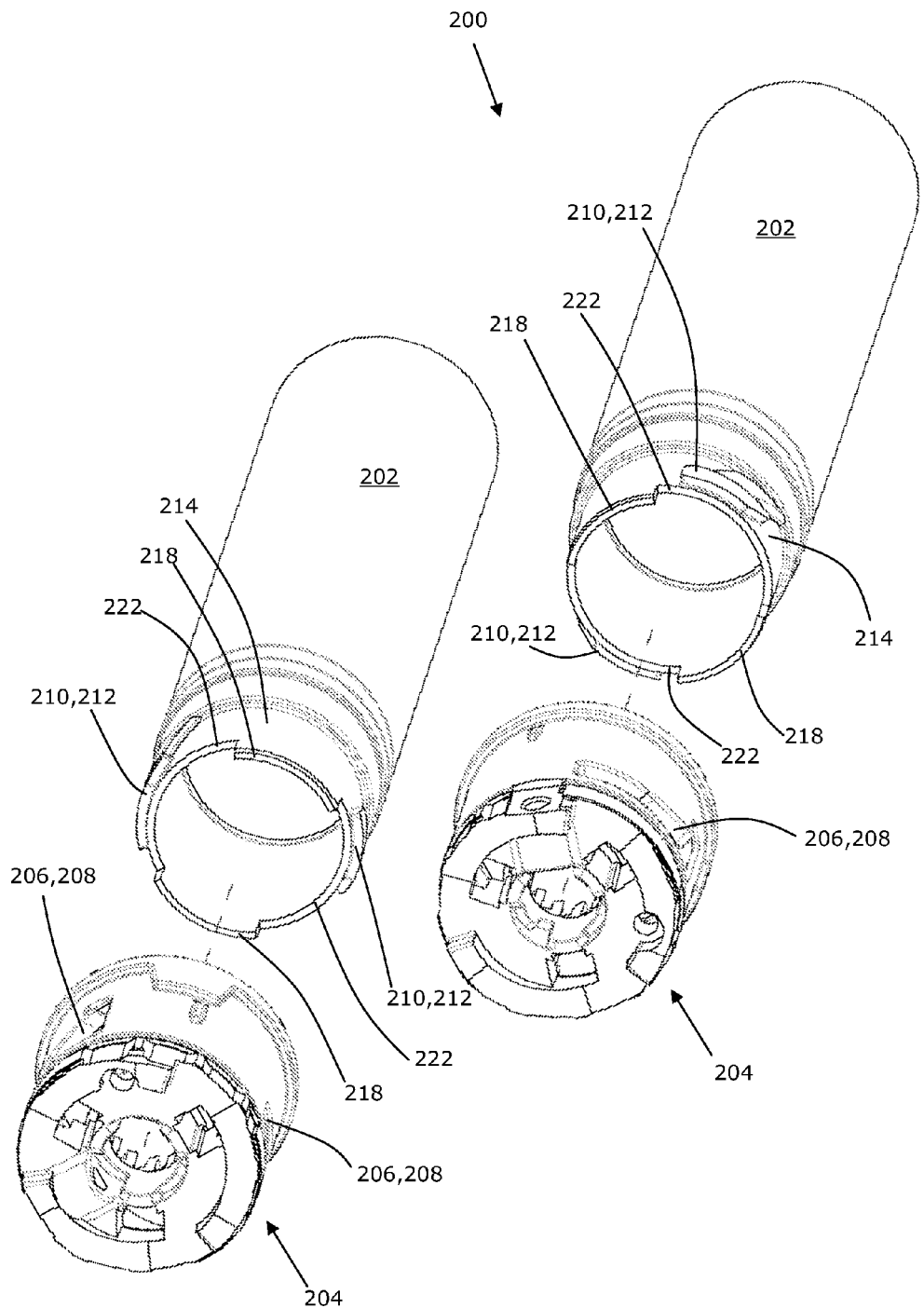
Figure 4:
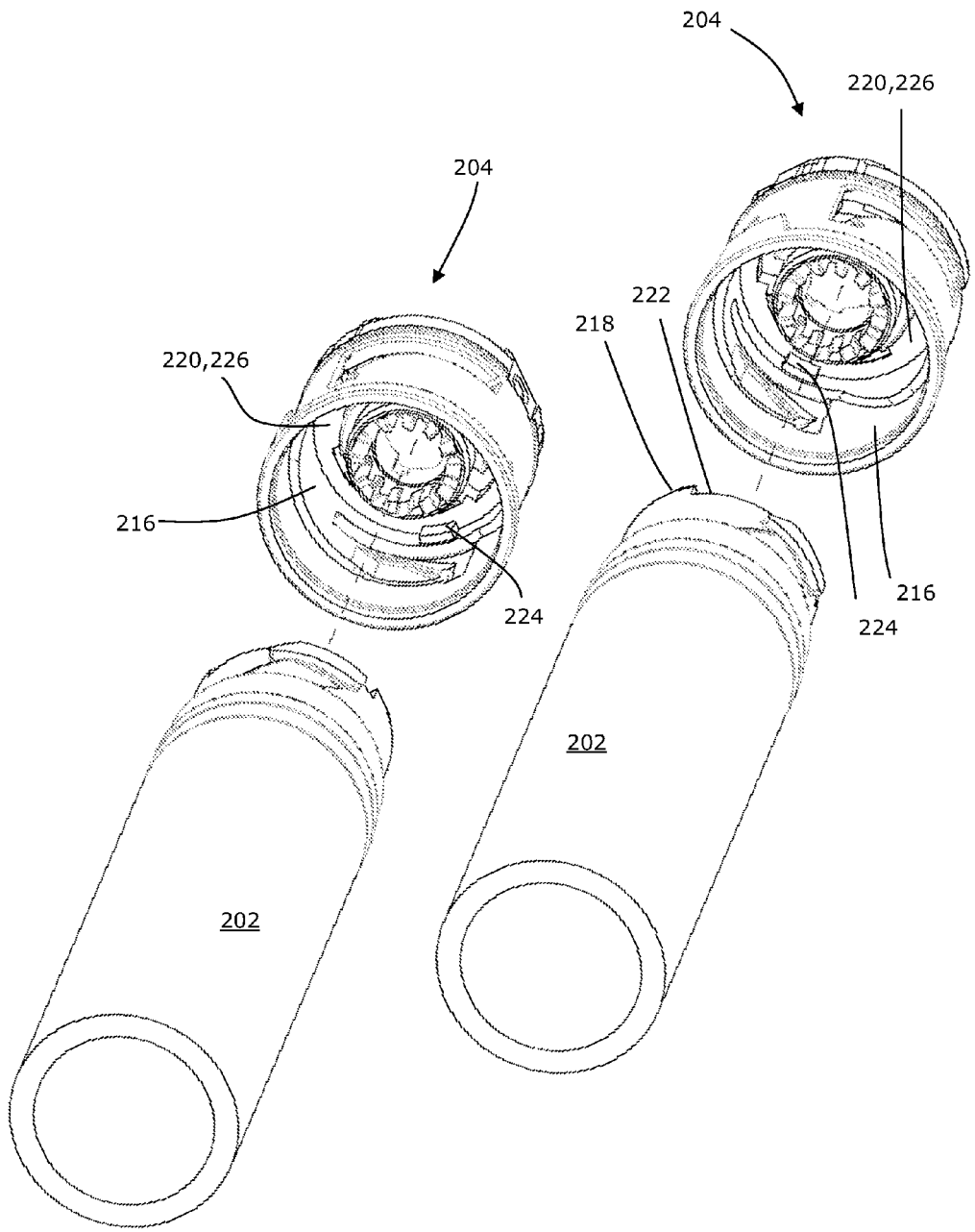
Figure 5:
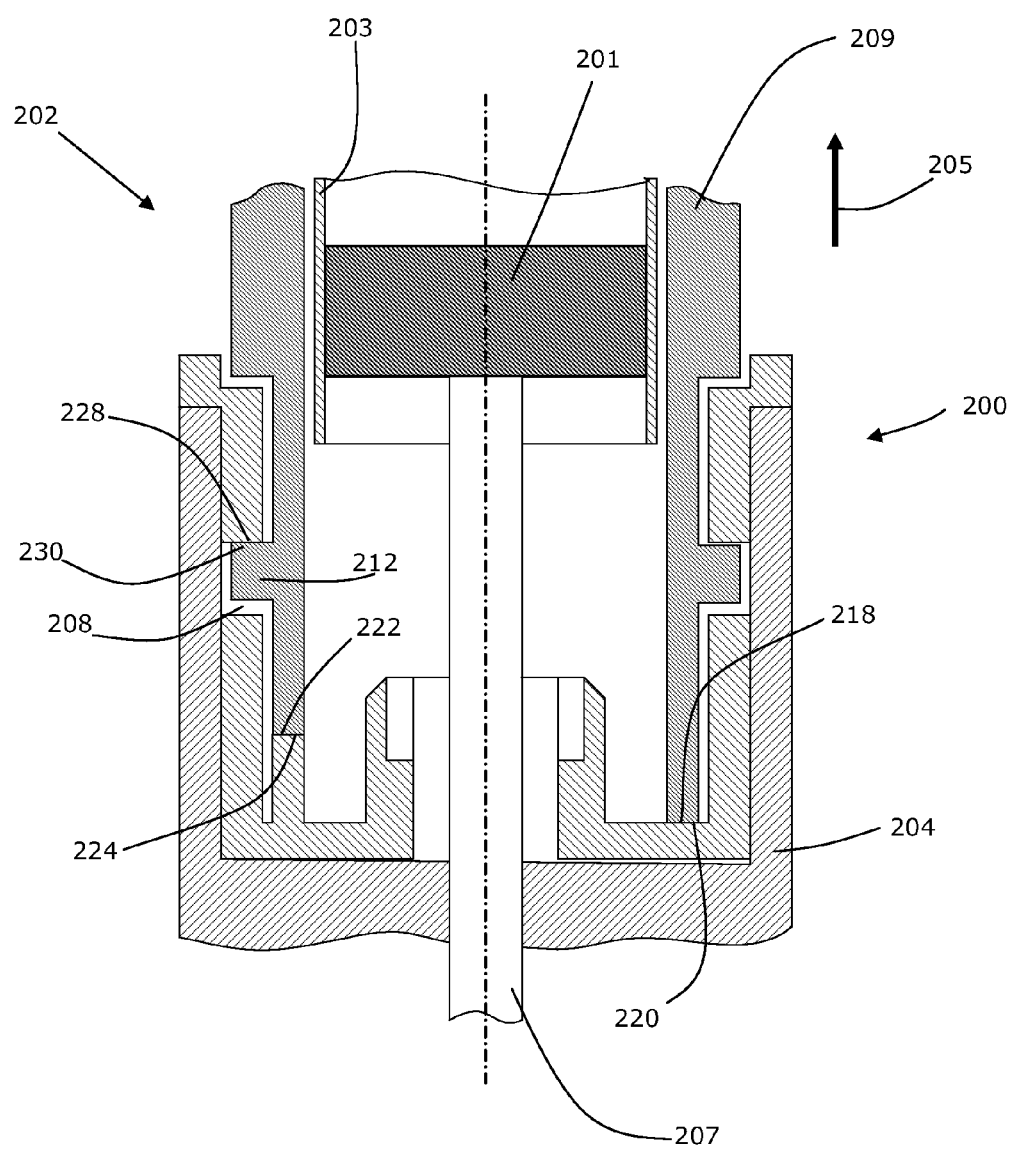
Figure 10:
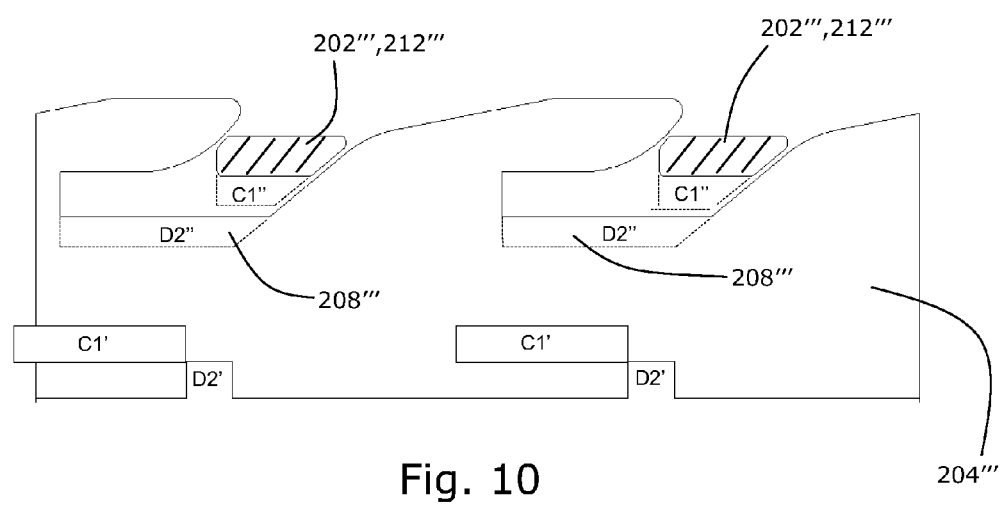
Figure 11A:
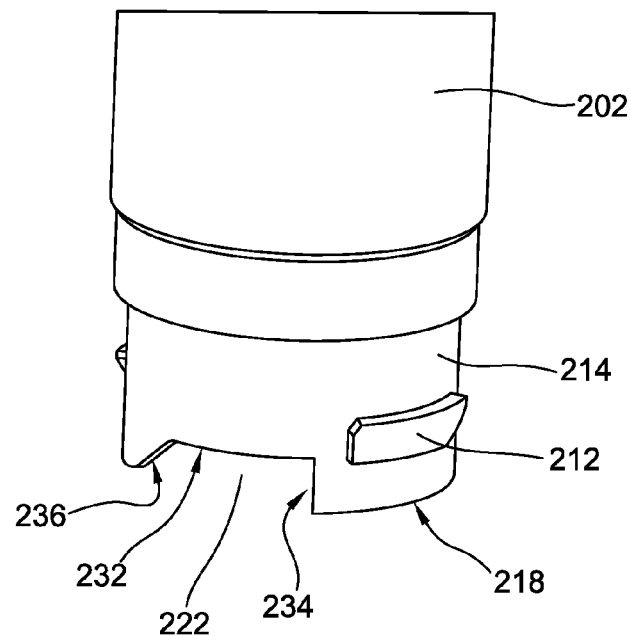
Figure 11B:
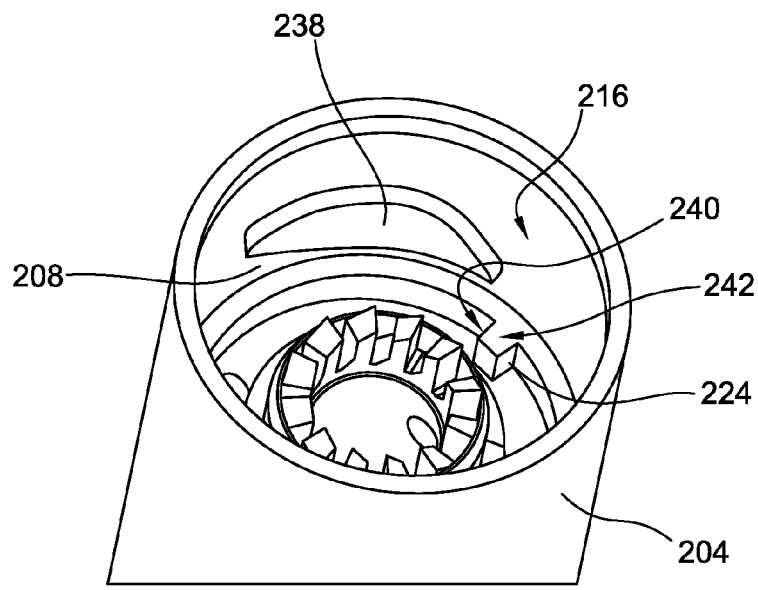

In the following the present invention is described in further detail with reference to the drawings in which:

FIGS. 1 and 2 disclose a syringe device known in the art,

FIGS. 3 and 4 disclose a container and a part of a dosing assembly according to the invention, FIG. 5 discloses a cross sectional view of a first and second coding mechanism, FIGS. 6-10 disclose different embodiments of the first and second coding mechanisms, and FIGS. 11a and 11b disclose an embodiment having axially extending indentations which during fastening are rotated into engagement with the axially extending protrusions.

FIGS. 1 and 2 disclose a syringe device 100 which prior to filing of the present application has been marketed in Europe and the USA by the applicant and under the name "NovoPen® 4". The syringe device 100 comprises a proximal part 102 and a distal part 104. In use, the proximal part 102 forms part of a dose setting unit (not shown) comprising a piston rod (not shown) extending through a passage (not shown) of the proximal part 102. A centre axis of the piston rod coincides with the dotted line 106. In use the distal part 104 defines a compartment 108 for accommodation of a reservoir (not shown) accommodating a medicament. The distal part 104 comprises two ridges 110 one on each side of the distal part which are used to secure the distal part 104 to the proximal part 102, by advancing the ridges 110 into matching tracks 112 of the proximal part 102. The tracks are defined on an inner surface 114 of the proximal part 102.

FIGS. 3 and 4 disclose a medical delivery system 200 comprising a container 202 and a dosing assembly 204 (for simplicity reasons only a part of the dosing assembly is shown in the drawings). The dosing assembly 204 defines a first fastening means 206 in the form of grooves 208 which during fastening of the container to the dosing assembly are engaged by second fastening means 210 which are defined by projections 212. Due to the shape of the grooves 208, the container is fastened to the dosing assembly through a concurrent axial and rotational movement of approximately 30 degrees. The projections 212 extent outwardly in a radial direction from a sidewall 214 of the container 202. The grooves are defined in a sidewall 216 of the dosing assembly 204 and extent from the surface of the sidewall and into the sidewall i.e. outwardly in a radial direction.

A first coding mechanism is defined by a coding geometry of each of the first and the second fastening means 206,210, whereby only predetermined dosing assemblies may be fastened to predetermined containers. The coding geometry is defined by the position of the projections and grooves and by the axial, radial and circumferential extent of the of the projections and grooves as will be described in further detail in relation to FIGS. 5-10.

Moreover, a second coding mechanism is defined by a proximal facing surface 218 of the container 202 and a corresponding distal facing surface 220 of the dosing assembly 204, the proximal end surface 218 of the container 202 defines two axially extending indentations 222 which during fastening of the container 202 to the dosing assembly 204 cooperates with two matching protrusions 224 of a distal facing coding surface 226 of the dosing assembly 204 so as to prevent said predetermined movement unless the proximal end surface 218 of the container 202 comprises said two axially extending indentations 222 and the distal end surface 220 of the dosing assembly 204 comprises said two matching protrusions 224.

FIG. 5 discloses a sectional view of the medical delivery system 200 wherein the container 202 is fastened to the dosing assembly 204, whereby the projections 212 of the second fastening means 210 of the container 202 are received by the grooves 208 of the first fastening means 206 of the dosing assembly 204. A proximal facing surface 228 of each of the grooves 208 engage a distal facing surface 230 of the corresponding projections 212. A proximal facing surface 218 of the container 202 define an axially extending indentation 222 which are adapted to receive a matching protrusion 224 extending from a distal facing surface 220 of the dosing assembly 204. The container 202 of FIG. 5 comprises a piston

201 which is slidingly received in a cartridge 203 of the container 202 and which is movable in a distal direction (indicated by arrow 205) by means of a driver 207 of the dosing assembly 204. The cartridge 203 is accommodated by in a cartridge holder 209 which defines the projections 212.

FIGS. 6-10 disclose different embodiments of first and second coding mechanisms of a medical device according to the invention. In each of the drawings the first and second coding mechanisms are illustrated as seen radially outward from the centre axis of the medical device—i.e. a 360 degrees view of the coding mechanisms is illustrated. For simplicity reasons the dosing assemblies and the containers are not illustrated in full. Elements of the container are hatched and elements of the dosing assembly are not hatched.

FIGS. 6-9 discloses two different dosing assemblies 204', 204" and two different containers 202',202". The containers in FIGS. 6 and 7 are identical and the containers in FIGS. 8 and 9 are identical. Furthermore, the dosing assemblies in FIGS. 6 and 8 are identical and the dosing assemblies in FIGS. 7 and 9 are identical. As it will be described further in detail below, the first container 202' may be fastened to the second dosing assembly 204" and the second container 202" may be fastened to the first dosing assembly 204' but not vice versa.

FIG. 6 discloses the first container 202', wherein the projections 212' are received in the grooves 208 ' of the dosing assembly 204'. Due to the shape of the grooves 208', the container 202' follows a concurrent axial and rotational movement relative to the dosing assembly 204', in order to be fastened to the dosing assembly 204'. However, due to the position of the indentations 222' defined (as indicated by dotted lines) in the proximal facing surface 218' of the container, and due to the position of the protrusion 224' (shown as D1) of the dosing assembly, the container 202' and the dosing assembly 204' are prevented from being fastened to each other (indicated by crossed-out arrow 234) as the surface 217' (also the facing surface of C1 with D1) of the indentation 222' will abut a surface 225' of the projection 224' (also shown as D1).

In FIG. 7 the container 202' and the dosing assembly 204" may be fastened to each other as indicated by arrow 236. Again due to the shape of the grooves 208', the container 202' will follow a concurrent axial and rotational movement relative to the dosing assembly 204' when the container is fastened to the dosing assembly. When the projections 212' are moved into the grooves 208", the protrusions 224" (also shown as D2) are moved into the indentations 222'. However, contrary to FIG. 6 the projections 224" (also shown as D2) and indentations 222' are located so as to allow the container and the dosing assembly to be fastened to each other.

FIG. 8 is similar to FIG. 7 in that the container and the dosing assembly are adapted to be fastened to each other, as indicated by arrow 236. When the projections 212" are moved into the into the grooves 208', the protrusions 224' (also shown as D1) are moved into the indentations.

FIG. 9 is similar to FIG. 6 in that the container and the dosing assembly cannot be fastened to each other, as indicated by crossed-out arrow 234. When the projections 212" are moved into the grooves 208", the projections 224" (also shown as D2) are moved into indentations 222". However, during the movement the surfaces 217" (also the facing surface of C2 with D2), 225" of the indentation 222" and the projection 224" (also shown as D2) will abut and prevent further relative rotation of the dosing assembly 204" and the container 202".

FIG. 10 discloses an alternative wherein the axial dimension of the projections 212''' are larger (as indicated by the dotted lines) than those in FIGS. 6-9. Similarly, the axial dimensions of the grooves 208''' (also shown as D2") are larger. Accordingly, the container 202''' of FIG. 10 cannot be received into the grooves 208',208" of the dosing assemblies 204',204" depicted in FIGS. 6-9, as the grooves 208',208" are too narrow in the axial direction to receive the projections 212'''. Although, the projections 212',212" of the containers 202',202" of FIGS. 6-9 may be received into grooves 208''' (also shown as D2") of the dosing assembly 204''' of FIG. 10, the user will recognize the slack between the axially thin projections 212',212" and the axially wide grooves 208'''. With the slack the user will immediately know that the dosing assembly 204''' and the container 202',202" are not adapted to be used together.

The container 202 of FIG. 11*a* is adapted to be fastened to the dosing assembly 204 of FIG. 11*b*, through a combined rotational and axial movement. The container 202 defines a radially extending projection 212 which extends from a sidewall 214 of the container 202, and an indentation 222 extending axially into the sidewall 214, in a distal direction from the surface 218. The axially extending indentation 222 defines a bottom surface 232, a stop surface 234 and an inclined surface 236. The dosing assembly 204 defines a groove 208 for receiving the projection 212 during fastening of the container 202 to the dosing assembly 204. In the embodiment of FIG. 11*b* the groove 208 is defined by a projection 238 extending radially out from a sidewall 216 of the dosing assembly 204 and in the direction of the centre of the dosing assembly 204. The inclined surface 236 is shaped so as to allow the axially extending protrusion 224 of the dosing assembly 204 to be moved into (and thus received by) the axially extending indentation 222 of the container 202. The stop surface 234 of the indentation 222 is adapted to engage a corresponding stop surface 240 of the protrusion 224 of the dosing assembly 204 so as to prevent further relative rotation between the container 202 and the dosing assembly 204. Abutment between the two stop surfaces 234,240 provides the user with a tactile indication of the fact that the container 202 is fastened to the dosing assembly 204.

The projection 238 of the dosing assembly is shaped such that the groove 208 does not define a stop surface and thus a dosing assembly similar to that of FIG. 11*b* but without the axially extending protrusion 224, will not provide the user with a tactile indication of the fact that the container 202 is fastened to such a dosing assembly 204. Accordingly, the container 202 of FIG. 11*a* cannot be fastened to a dosing assembly 204 similar to that of FIG. 11*b* but not defining the protrusion 224. This prevents a container 202 from being fastened to a dosing assembly 204 of that configuration.

Containers similar to that of FIG. 11*a* but not defining the axially extending indentation 222 may take two forms. A first form wherein the proximal end surface 218 is defined at the same axial level as the surface 218 in FIG. 11*a*, and a second wherein the proximal end surface 218 is defined at the same axial level as the bottom surface 232 in FIG. 11*a*. The difference between the first and the second forms is the distance between surface 218 and the projection 212.

A container 202 of the first form i.e. wherein the proximal end surface 218 is defined at the level of the proximal end surface 218 of FIG. 11*a* and without indentations 222, cannot be fastened to the dosing assembly 204 of FIG. 11*b* as the proximal end surface 218 of the container 202 will abut a distal facing surface 242 of the protrusion 224, whereby the projection 212 cannot be received in the groove 208 or can only be moved partly into the groove 208 i.e. in a way insufficient to fasten the container 202 to the dosing assembly 204.

A container 202 of the second form i.e. wherein the proximal end surface 218 is defined at the level of the bottom surface 232 in FIG. 11a and not defining indentations 222, cannot be fastened to a dosing assembly 204 not defining the axially extending protrusion(s) 224 as the user is not provided with the tactile indication allowing him to determine when the container 202 is fastened to the dosing assembly 204 and vice versa. Accordingly, the user will continue the relative rotation between the container 202 and the dosing assembly 204, whereby the projection 212 will be moved out of the groove 208, such that the container 202 is not fastened to the dosing assembly 204.

It will be appreciated from the above, that the embodiment of FIG. 11a and 11b increases user safety as a container 202 not designated to be used in connection with a predetermined dosing assembly 204 cannot be fastened to such a dosing assembly 204. Thus, the user is prohibited from attaching a container 202 with a wrong medicament or a correct medicament in a wrong concentration to a dosing assembly 204, and thereby prevented from ejecting such a medicament.

The invention claimed is:

1. A medical delivery system comprising:
    a container having a second fastening means and adapted to contain a medicament in a chamber defined by the container and a slidably arranged piston which is moveable in a distal direction towards an outlet so as to reduce the volume of the chamber and expel the medicament through the outlet, the container comprising a proximal part having a circular side wall defining a proximal circular end surface;
    a dosing assembly adapted to be fastened to the container, so as to allow a driver of the dosing assembly to move the piston of the container in the distal direction;
    wherein the dosing assembly defines a first fastening means which during fastening of the container to the dosing assembly engages the second fastening means of the container whereby the container is fastened to the dosing assembly through a predetermined movement defined by at least one of the first and the second fastening means, at least a part of said predetermined movement being a concurrent axial and rotational movement which is less than one revolution;
    wherein a sidewall of one of the first and second fastening means defines at least one projection extending in a radial direction, each of the at least one projection being adapted to engage a corresponding groove defined in a sidewall of the other one of the first and second fastening means;
    wherein a first coding mechanism is defined by a coding geometry of each of the first and the second fastening means, the first coding mechanism being adapted to prevent said predetermined movement unless each of the first and the second fastening means defines a predetermined coding geometry; and
    wherein the coding geometry is selected from a predetermined group of coding geometries; and
    wherein the system further comprises a second coding mechanism defined by one or more protrusions and/or indentations arranged along the proximal end surface of the container, and mating one or more corresponding indentations and/or protrusions at the distal end surface of the dosing assembly.

2. A medical delivery system according to claim 1, wherein the proximal end surface of the container defines one or more axially extending protrusions and/or indentations which during fastening of the container to the dosing assembly cooperate(s) with corresponding one or more indentations and/or protrusions of a distal facing coding surface of the dosing assembly so as to prevent said predetermined movement unless each of the distal and proximal facing coding surfaces define one or more predetermined indentations and/or protrusions selected from a predetermined group of indentations and/or protrusions.

3. A medical delivery system according to claim 2, wherein the container comprises at least two protrusions extending from the proximal end surface of the container and the dosing assembly comprises at least two indentations adapted to cooperate with the at least two protrusions.

4. A medical delivery system according to claim 1, wherein the predetermined movement defines a substantially pure axial movement and followed by the concurrent axial and rotational movement.

5. A medical delivery system according to claim 1, wherein the predetermined movement defines the concurrent axial and rotational movement and a subsequent substantially pure rotational movement.

6. A medical delivery system according to claim 1, wherein the first and/or second coding mechanism is/are adapted to prevent at least a part of the axial and/or rotational movement of the predetermined movement, so as to prevent coupling of the container to the dosing assembly.

7. A medical delivery system according to claim 1, wherein the coding geometry of the first coding mechanism is defined by at least one of: a circumferential extent of the first and second fastening means, an axial extent of the first and second fastening means, a radial extent of the first and second fastening means, and the circumferential position of the first and second fastening means.

8. A medical delivery system according to claim 1, wherein the container comprises a cartridge holder defining said indentation and/or protrusion, and a cartridge defining said chamber, and wherein the cartridge is non-detachably attached to the cartridge holder.

9. A medical delivery system according to claim 1, comprising:
    a first container adapted to be fastened to a first dosing assembly; and
    a second container adapted to be fastened to a second dosing assembly; and
    wherein the first and/or second coding mechanism of at least two of the first and second container and the first and second dosing assembly is/are adapted to prevent the first dosing assembly and second container from being fastened to each other, and to prevent the second dosing assembly and the first container from being fastened to each other.

10. A medical delivery system according to claim 9, wherein the predetermined movement required for coupling and uncoupling the first container to the first dosing assembly and for coupling the second container to the second dosing assembly are substantially the same.

11. A medical delivery system according to claim 1, wherein the at least one indentation and/or protrusion of the second coding mechanism of the dosing assembly is fixedly oriented in relation to the projection or groove of the first fastening means of the dosing assembly.

12. A container for a medical delivery system, the container being adapted to contain a medicament in a chamber defined by the container and a slidably arranged piston which is moveable in a distal direction towards an outlet so as to reduce the volume of the chamber and expel the medicament through the outlet, wherein:
    the container comprises a first coding mechanism defined by a fastening means for fastening the container to a dosing assembly by engaging corresponding fastening means of the dosing assembly, so as to allow a driver of the dosing assembly to move the piston of the container in the distal direction, the container comprising a proximal part having a circular side wall defining a proximal circular end surface;

the fastening means of the container defines one or more projections and/or grooves extending in a radial direction and being shaped so as to allow the container to be fastened to the dosing assembly through a predetermined movement, at least a part of said predetermined movement comprising a concurrent axial and rotational movement which is less than one revolution; and the fastening means of the container defines a coding geometry adapted to prevent said predetermined movement unless the fastening means defines a predetermined coding geometry selected from a predetermined group of coding geometries;

wherein the container further comprises a second coding mechanism defined by one or more protrusions and/or indentations arranged along the proximal circular end surface of the container for mating to one or more corresponding indentations and/or protrusions in a dosing assembly.

13. A container according to claim 12, wherein the container defines a proximal end surface defining one or more axially extending protrusions and/or indentations which during fastening of the container to the dosing assembly cooperate(s) with corresponding one or more indentations and/or protrusions of the dosing assembly so as to prevent said predetermined movement unless the said protrusions and/or indentations of the container define(s) one or more predetermined indentation(s) and/or protrusion(s) from a predetermined group of indentation(s) and/or protrusions.

14. A container according to claim 13, wherein the container comprises at least two protrusions extending from the proximal end surface of the container.

15. A container according to claim 12, wherein the predetermined movement defines a substantially pure axial movement and followed by the concurrent axial and rotational movement.

16. A container according to claim 12, wherein the predetermined movement defines the concurrent axial and rotational movement and a subsequent substantially pure rotational movement.

17. A container according to claim 12, wherein at least one of the one or more projections and/or grooves, and the one or more axially extending protrusions and/or indentations, is adapted to prevent at least a part of the axial and/or rotational movement of the predetermined movement, so as to prevent coupling of the container to the dosing assembly.

18. A container according to claim 12, wherein the coding geometry is defined by at least one of: a circumferential extent of the fastening means, the axial position of the fastening means, an axial extent of the fastening means, a radial extent of the fastening means,. and the circumferential position of the fastening means.

19. A dosing assembly for a medical delivery system, the dosing assembly comprising:

a driver;

a fastening means for fastening the dosing assembly to a container for accommodation of a medicament by engaging corresponding fastening means of the container, so as to allow the driver of the dosing assembly to move a piston of the container in the distal direction;

wherein the fastening means of the dosing assembly defines one or more projections and/or grooves extending in a radial direction and being shaped so as to allow the container to be fastened to the dosing assembly through a predetermined movement, at least a part of said predetermined movement comprising a concurrent axial and rotational movement which is less than one revolution;

wherein the fastening means of the dosing assembly defines a first coding geometry adapted to prevent said predetermined movement unless the fastening means defines a predetermined coding geometry selected from a predetermined group of coding geometries;

wherein the dosing assembly further includes a distally facing cavity defined by a circumferential side wall, the distally facing cavity being further defined by a distal bottom surface, the cavity being structured to receive a proximal end portion of the container; and wherein the distally facing cavity further comprises a second coding geometry defined by one or more indentations and/or protrusions arranged along the circumferential side wall and extending axially relative to the distal bottom surface of the distally facing cavity.

20. A dosing assembly according to claim 19, wherein the dosing assembly which defines a distal surface defining one or more axially extending indentations and/or protrusions which during fastening of the container to the dosing assembly cooperate(s) with matching one or more protrusions and/or indentations of the container so as to prevent said predetermined movement unless the indentations and/or protrusions of the dosing assembly define one or more predetermined indentations and/or protrusions.

21. A dosing assembly according to claim 19, wherein the predetermined movement defines a substantially pure axial movement and followed by the concurrent axial and rotational movement.

22. A dosing assembly according to claim 19, wherein the predetermined movement defines the concurrent axial and rotational movement and a subsequent substantially pure rotational movement.

23. A dosing assembly according to claim 19, wherein at least one of the one or more projections and/or grooves, and the axially extending protrusions and/or indentations, are structured to prevent at least a part of the axial and/or rotational movement of the predetermined movement, so as to prevent coupling of the container to the dosing assembly.

24. A dosing assembly according to claim 19, wherein the coding geometry is defined by at least one of: a circumferential extent of the fastening means, the axial position of the fastening means, an axial extent of the fastening means, a radial extent of the fastening means, and the circumferential position of the fastening means.

* * * * *